(12) United States Patent
Rockley

(10) Patent No.: US 6,605,054 B2
(45) Date of Patent: *Aug. 12, 2003

(54) MULTIPLE BYPASS PORT PHACO TIP

(75) Inventor: Paul W. Rockley, Laguna Niguel, CA (US)

(73) Assignee: Advanced Medical Optics, Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/073,371

(22) Filed: Jan. 30, 2002

(65) Prior Publication Data

US 2002/0091351 A1 Jul. 11, 2002

Related U.S. Application Data

(63) Continuation-in-part of application No. 09/675,339, filed on Sep. 28, 2000, which is a continuation-in-part of application No. 09/163,985, filed on Sep. 30, 1998, now Pat. No. 6,033,376.

(51) Int. Cl.7 ................................................. A61B 17/20
(52) U.S. Cl. .............................. 604/22; 604/35; 604/43
(58) Field of Search ............................. 604/20, 22, 35, 604/27, 43

(56) References Cited

U.S. PATENT DOCUMENTS

| 5,024,654 A | 6/1991 | Tyler |
| 5,282,786 A | 2/1994 | Ureche |
| 5,354,265 A | 10/1994 | Mackool |
| 5,505,693 A | 4/1996 | Mackool |
| 5,603,703 A | 2/1997 | Elsberry et al. |
| 5,741,226 A | 4/1998 | Strukel et al. |
| 5,873,851 A | 2/1999 | Nilsson |
| 6,033,376 A | 3/2000 | Rockley |
| 6,126,629 A | 10/2000 | Perkins |
| 6,398,754 B1 * | 6/2002 | Sutton et al. .................. 604/22 |

FOREIGN PATENT DOCUMENTS

JP    P2000-237228 A    9/2000

* cited by examiner

Primary Examiner—Brian L. Casler
Assistant Examiner—Jeremy Thissell
(74) Attorney, Agent, or Firm—Walter A. Hackler; Peter Jon Gluck

(57) ABSTRACT

Phaco tip apparatus for a phacoemulsification/irrigation and aspiration handpiece having a drive assembly including a needle having a tip for emulsifying a cataractic lens and a lumen communication with primary and a secondary aspiration ports for aspirating emulsified lens. A sleeve establishes an annular passage around the needle and enables irrigation fluid to pass into an eye through a cornea/sclera wound while cooling the needle. A bypass port, disposed in said needle and under said compressible sleeve, establishes fluid communication between the lumen and the annular passage in order to enable irrigation fluid to pass into said lumen upon clogging of the primary and secondary aspiration ports, thus providing fluid surge protection. A depending member may be disposed within said compressible sleeve limits compression of opposing walls of said compressible sleeve in order to prevent contact of said compressible sleeve with the needle, maintain the annular passage flow of irrigation fluid past the needle and prevent the compressible sleeve from closing the bypass port.

9 Claims, 1 Drawing Sheet

MULTIPLE BYPASS PORT PHACO TIP

The present application is a continuation-in-part of U.S. Ser. No. 09/675,339 filed Sep. 28, 2000, which is a continuation-in-part of U.S. Ser. No. 09/163,985 filed Sep. 30, 1998, now U.S. Pat. No. 6,033,376.

The present invention generally relates to phacoemulsification handpieces for the removal of a cataract lens from an eye and is more particularly related to phaco tip apparatus for a phacoemulsification handpiece. A well known method for the removal of a cataract through a surgical incision in the eye is known as phacoemulsification. A handpiece for phacoemulsification generally includes an ultrasonic or sonic generator which is attached to a hollow needle which is vibrated and, when inserted into an eye, is capable of emulsifying an eye lens and aspiration thereof through a lumen in the needle. The needle is surrounded by a sleeve when inserted through an incision in the eye. The tip of the needle engages and emulsifies the cataract and a suction force is applied through the needle interior lumen to withdraw the emulsified cataract into the needle and out of the eye.

The sleeve protects the wound through which the needle is passed from contacting the needle which can become heated, and the sleeve further establishes an annular passage around the needle for providing an irrigation fluid to the eye, while at the same time cooling the needle.

Typically, the cornea or sclera incision is linear and has a length approximately to one-half the circumference of the sleeve in order to minimize fluid leakage from the incision, or wound, when the needle/sleeve is inserted therethrough.

A great number of sleeve designs have been proposed and a number of materials have been utilized in prior art sleeves. For example, U.S. Pat. No. 4,787,889 to Steppe et al, discloses a flexible sleeve made of a synthetic resin such as silicon rubber which is able to fold back or telescope when inserted through an incision. The problems with these prior art devices include collapsing of the flexible sleeve in the area of the wound by pressure from surrounding tissue. This collapsing of the sleeve blocks flow of the irrigation to the surgical site and around the vibrating needle, which can cause overheating and damage to adjacent tissue. Sleeves made out of metallic material, such as also described in the hereinabove referenced U.S. patent, do not allow collapse and, accordingly, allow a greater amount of fluid leakage from the wound.

In order to minimize leakage from the wound past the sleeve, an elliptical sleeve has been proposed, for example, see U.S. Pat. No. 5,084,009. This collapsible, or compressible, sleeve is made with a shape matching the configuration of a surgical incision in order to minimize leakage between the exterior surface of the sleeve and the surgical incision. However, in order for the ultrasonic needle to exhibit a desired and vibratory motion, which is relatively free from damping, this elliptical sleeve must be prohibited from touching the needle during the operation.

During phacoemulsification procedures, the needle must be partially rotated and its angle of incident changed in order to effect complete phacoemulsification and removal of the lens. In these procedures, a soft sleeve, particularly one shaped to the size of the wound, may collapse, or deflect against the ultrasonic needle. When the sleeve is pushed against the rapidly vibrating needle, the needle and sleeve tend to overheat due to friction, which may damage delicate cornea or sclera tissue, particularly the corneal epithelium.

Also during phacoemulsification procedures, an emulsified lens particle may block the aspirating lumen. The blockage may be sufficient to require reversal of fluid flow through the lumen in order to dislodge the blockage. This interruption may cause undesirable pressure changes in the eye. Many equipment designs and methods have been derived in order to minimize the problems introduced by a blocked aspiration lumen. Among such designs is the use of a bypass port between the irrigation fluid in the sleeve and the aspiration lumen of the needle. Such a port enables irrigation fluid to be aspirated when the primary port is occluded to prevent surge to the eye.

Unfortunately, when such a bypass port is used in conjunction with a compressible sleeve, inadvertent closure of the port may occur.

The present invention is directed to a sleeve which shapes itself to the wound by pressure of surrounding tissue in order to minimize leakage of fluid therepast. In addition, internal structure of the sleeve maintains proper annular channel around the needle for passage of cooling fluid. Accordingly, the needle is prevented from touching the sleeve. In addition, the sleeve is attached to the phacoemulsification handpiece to enable angular motion of the needle within the sleeve so that the sleeve wound junction is not disturbed. Further structure is provided to prevent any closure of a bypass port as hereinabove noted.

In one embodiment of the present invention, multiple ports are provided with one of the ports outside the sleeve and another under the sleeve as herein above noted.

SUMMARY OF THE INVENTION

Phaco tip apparatus in accordance with the present invention is suitable for a phacoemulsification handpiece having an ultrasonic drive assembly for emulsifying and aspirating a cataract lens through a cornea/sclera wound.

The subject phaco tip apparatus generally includes a needle having a tip, for emulsifying a cataract lens through a cornea/sclera wound, and lumen through the tip to provide a primary aspiration port for aspirating emulsified lens. A sleeve provides a means for establishing an annular passage around the needle and enabling the irrigation fluid to pass into an eye through the cornea/sclera wound while simultaneously cooling the needle. The sleeve may be compressible as hereinafter described.

A bypass port is disposed in the needle and beneath the compressible sleeve for establishing fluid communication between the lumen and the annular passage in order to enable irrigation fluid to pass into the needle lumen upon clogging, or blocking of the primary port of the tip. Thus, the bypass port protects, or lessens, any surge of fluid and/or fluid negative pressure in the eye when the primary port is unblocked.

In addition, a secondary aspiration port may be provided and disposed in the needle between the needle end and the sleeve for enabling continued aspiration of fluid upon clogging of the primary aspiration port.

The sleeve when compressible, preferably includes a wall configuration which provides a means for controlling compression of the sleeve in order to cause the compressible sleeve to shape and conform to the cornea/sclera wound and limit fluid egress from the wound. That is, the construction of the compressible sleeve wall enable the sleeve, upon compression by tissue subtending the wound, to fill, or contact, all of the wound surface so that no gaps are established which can permit the leakage of fluid.

In addition, a hub means may be provided for attaching the compressible sleeve to the handpiece and for enabling the needle to be angularly displaced within the compressible sleeve means. Thus, once the compressible sleeve is conformed to the wound shape, it need not be disturbed by subsequent manipulation of the needle which is necessary in order to properly emulsify and aspirate a cataract lens.

In one embodiment of the invention, the compressible sleeve includes a variation in wall thickness around the circumference of the compressible sleeve which may include two areas of the sleeve wall having greater thickness than adjoining areas in the sleeve wall. These two areas are preferably spaced apart from one other at about 180° around the sleeve means circumference. Thus, when the compressible sleeve is inserted into a slit type cornea/sclera wound, the thicker portions of the wall are disposed at opposite ends of the slit and compression of the sleeve enables confirmation of the sleeve with all of the surrounding wound tissue including the ends of the slit.

Still more particularly, the two areas of greater wall thickness may include nodules which extend outward from the compressible sleeve means.

In another embodiment of the present invention, the sleeve may include a variation in wall density of the sleeve walls around the circumference of the sleeve. The variation in wall density preferably includes two areas of the sleeve having a lower density than adjoining areas of the sleeve wall, with the two areas of lower density being spaced apart from one another at 180° around the sleeve means configuration.

In a manner as similarly described in conjunction with a wall having thicker areas, this lower density area enables a preferential compression of the sleeve and outward extension of the sleeve in a low density wall areas so that the sleeve can conform and contact with all of the tissue surrounding the slit wound.

Also, in accordance with the present invention, in order to limit compression of opposing walls of the compressive sleeve to prevent contact of the compressible sleeve with the needle, and undesired closure of the bypass port at least one depending member is provided. In addition to prevention contact of the compressible sleeve with the needle, and closure of the bypass port by the compressive sleeve, continued cooling of the needle is ensured at all times.

More particularly, two depending members having a length greater than the diameter of the needle, may be disposed within the compressible sleeve and are attached to opposing walls between the two wall areas of greater thickness, or lesser density.

BRIEF DESCRIPTION OF THE DRAWINGS

The present invention may be more clearly appreciated when taken in conjunction with the accompanying drawings, in which.

DETAILED DESCRIPTION

Figure 1:
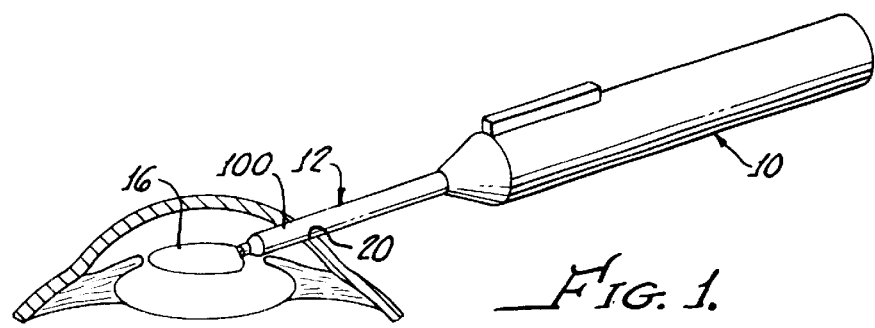
FIG. 1 is a perspective view of a phacoemulsification handpiece using the phaco tip apparatus in accordance with the present invention as it may be inserted through a cornea/sclera wound for the removal of a cataract lens from a lens capsule.

With reference to FIG. 1, there is shown a phacoemulsification handpiece 10 utilizing sleeve apparatus 12 in accordance with the present invention for removing a cataract lens 16 by emulsification/aspiration through a cornea/sclera wound 20. The phaco handpiece, or instrument 10, may be of any conventional type operating, as is well known to those skilled in the art, except as modified with the phaco tip apparatus 12 in accordance with the present invention.

Figure 2:
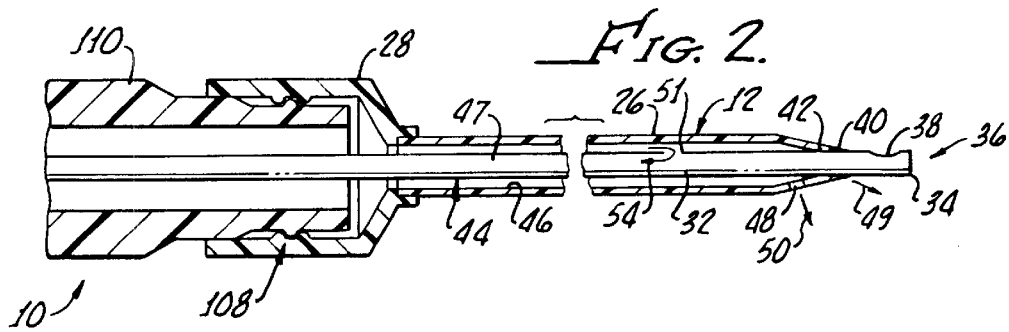
FIG. 2 is a cross-sectional view of the phaco tip apparatus in accordance with the present invention including a needle with a lumen aspiration of emulsified lens through a primary aspiration port, a secondary aspiration port along with a bypass port therein, a compressible sleeve and a hub for attaching the sleeve and needle to the phacoemulsification handpiece.

As more clearly shown in FIG. 2, the sleeve apparatus 12 in accordance with the present invention includes a sleeve 26 and a hub 28 fixed thereto. It should be appreciated that the sleeve 26 and hub 28 may be formed from the same type of material, for example, a silicone or silicone-type material or of a thermoplastic polyurethane and that the sleeve 26 and the hub 28 may be either fixed to one another or formed integrally.

The handpiece 10 includes a sonic or ultrasonic drive assembly, not shown, attached to a hollow needle 32, which includes a primary aspiration port 34 in an end 36 of the needle 32 and at least one secondary port aspiration 38 disposed proximate the end 36 of the needle 32. The end 36, including the secondary aspiration port, protrudes through the sleeve 26 at a sleeve distal end 40 with a flexible seal 42 disposed there between.

The secondary aspiration port 38, being disposed outside the sleeve 26 between the needle end 34 of sleeve enables continued aspiration of emulsified lens upon clogging of the primary aspiration port.

As shown, an annular passage 44 is established between an inside surface 46 of the sleeve 26 and an outside surface 47 of the needle 32 in order to enable irrigation fluid provided by the handpiece 10 to pass around the needle 32 and past the flexible seal 42 or a port 48 in a conventional manner as represented by the arrows 49–50 respectively. The fluid interconnection between the annular passage 44 and the handpiece is not shown, as this arrangement is well known in the area.

A bypass port 51 in the needle under the sleeve 26 establishes fluid communication between the needle lumen 52 and the annular passage 44 in order to enable irrigation fluid to pass into the lumen 52, as indicated by an arrow 54, upon partial clogging of the primary aspiration port 34 or total clogging of the primary and secondary aspiration ports 34, 38. Thus, providing fluid surge protection. There may be a small amount of fluid transferred between the annular passage 44 and lumen 52 during normal, unblocked aspiration, but this fluid flow is not important in the overall operation of the phaco tip 12.

It has been found that for a needle diameter of 1.1 mm with a lumen having a cross-sectional area of the secondary aspiration port 38 should be between about 5% and about 15% of the cross-sectional area of the lumen 52. The cross-sectional area of the bypass port 50 should be between about 5% and about 15% of the cross-sectional area of the line 52.

Figure 3:
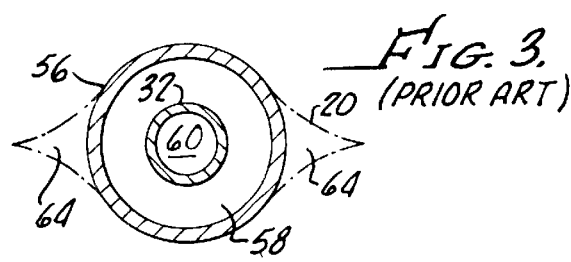
FIG. 3 is a cross-sectional view of a prior art sleeve as inserted into a slit type wound illustrating the problem with regard to gaps being created by such insertion which provide a means for fluid egress from the eye during the phacoemulsification procedure.

It is important, during a phacoemulsification procedure, that tissue surrounding the cornea/sclera wound 20 not be damaged, particularly the epithelium layer under the cornea. Since damage to this tissue may occur due to heating, a prior art sleeve 56, see FIG. 3, has been typically provided with sufficient resiliency in order to prevent total collapse of the sleeve 56 in order to maintain a fluid conduit 58 between the sleeve 56 and the needle 32. While aspiration of cataractic tissue, not shown, is performed through a needle lumen 60, sufficient cooling is only provided by the irrigation of fluid passing through the passage 58. It must also be appreciated that this size of the needle 32 and sleeve 58 is quite small, since the length of the slit cornea/sclera wound may be only about 3 mm.

Not only is it important that the passage 58 be maintained for cooling of the needle, it is also important that the needle 32 does not contact the sleeve 56 because conductive heat transfer to the tissue surrounding the wound 20 would cause undesired heating. Also, a collapsed sleeve 26 may cause closure of the bypass port 50 which would defeat its intended operation.

The rigidity or relative rigidity of the prior art sleeve 56, as is necessitated by the constraints hereinabove set forth, preclude the sleeve 56 from shaping, or conforming, to the slit wound 20. Rather, gaps 64 between the sleeve 56 and the wound 20 occur which enable leakage of irrigation fluid therepast. This leakage is undesirable, as is well known in the art, because it interferes with proper maintenance of ocular pressure during the phacoemulsification procedure.

Figure 5:
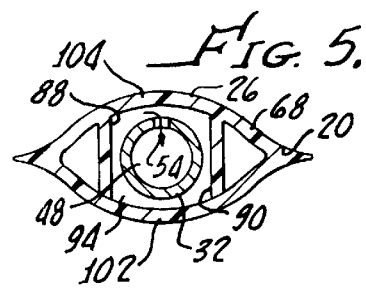
FIG. 5 is the collapsible sleeve as shown in FIG. 4 shown inserted into a slit type cornea/sclera wound, with the outside, or perimeter, of the collapsible sleeve conforming exactly to the slit opening upon compression of the sleeve so that little or no gaps are established for the egress of fluid.
Figure 4:
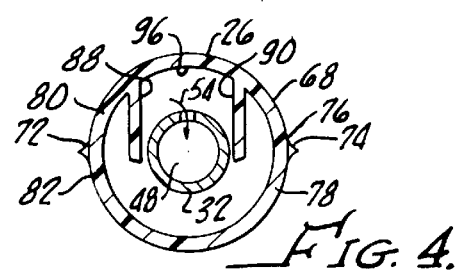
FIG. 4 is a cross-sectional view of one embodiment of the present invention showing a compressible sleeve having side wall of greater thickness disposed in an opposing relationship around the compressible sleeve along with a pair of depending members which are provided for limiting the collapse of the collapsible sleeve and along with a pair of depending members which are provided for limiting the collapse of the collapsible sleeve and preventing closure of the bypass port.

As shown in FIGS. 4 and 5, the sleeve 26 in accordance with the present invention, overcomes the deficiencies of the prior art sleeve 56, by incorporating a sleeve wall which provides a means for controlling compression of the sleeve 26 in order to cause the compressible sleeve 26 to shape and conform to the cornea/sclera wound 20, thus limiting fluid egress from the wound, see FIG. 5.

Referring again to FIG. 4, a variation in sleeve wall 68 thickness is provided in two areas, 72, 74 around the sleeve 26 and preferably spaced apart from one another at a 180° angle in order to enable the sleeve 26 to shape and conform to the cornea/sclera wound 20 as shown in FIG. 5.

Because the areas 72, 74 are thicker than adjacent areas 76, 78, 80, 82, respectively, controlled collapse of the sleeve 26 under pressure of surrounding tissue, not shown in FIG. 4, is provided. In order to further enhance sealing between the sleeve 26 and the wound 20, the thicker areas may be in the form of nodules 72, 74. In this manner, the sleeve 26 completely shapes, or conforms, to the wound 20 as shown in FIG. 5.

In order to prevent the compression, or collapse of the sleeve 26 onto the needle 32 and closure of the bypass port 50, depending members 88, 90 are provided. With a length greater than a diameter of the needle 32, the depending members 88, 90 prevent contact of the sleeve 26 with the needle 32 maintain an annular passage 94 therebetween, see FIG. 5.

The depending members 88, 90 may be formed of the same material as the sleeve and integrally formed thereto. It should also be appreciated that the members 88, 90 need only be present on an inside of a surface 96 of the sleeve 26 in an area 100 of the sleeve passing through the wound 20, see FIG. 1.

The depending members 88, 90 may be attached to opposing walls 102, 104 of the sleeve 26 which will result in the same compressed configuration as shown in FIG. 5.

Because of the important conformation of the sleeve 26 with the wound 20, rotation of the sleeve within the wound 20 is not desirable. Accordingly, in order to enable the needle 32 to be angularly displaced within the compressible sleeve 26, the hub includes snap fittings 108 which enable rotation of the hub 28 and sleeve 26. Thus, the sleeve 26 may be held in an orientation affording proper shaping of the sleeve 26 with the wound 20, while the needle is angularly moved within the sleeve and further axially tilted within the wound 20 in order to effect a proper emulsification of the lens 16 and aspiration thereof through the needle lumen 60.

Figure 6:
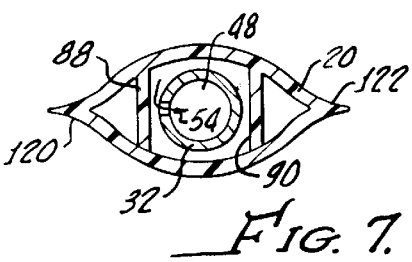
FIG. 6 is an alternative embodiment of the present invention in which side walls include a lower density in opposing walls for enabling preferential collapse of the collapsible sleeve and a bypass port disposed in the needle adjacent the dependant member.
Figure 7:
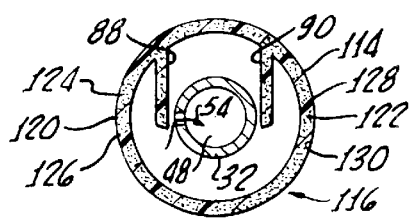
FIG. 7 shows the sleeve as shown in FIG. 6 as it conforms to a slit cornea/sclera wound.

As hereinabove discussed, it is important that the sleeve 26 includes wall means 68 for controlling compression of the sleeve 26 and in that regard, and alternate wall means 114 may be provided for an alternate sleeve 116 as shown in FIG. 6. In this embodiment, the wall 114 includes areas of a lower density 120, 122 surrounded by areas 124, 126, 128, 130 of heavier density which enables collapse of the sleeve upon compression by surrounding wound tissue so that the sleeve 116 takes the shape and conforms to the wound 20 as shown in FIG. 7. Hence, the many gaps, not shown, are not established between the sleeve 116 and the wound 20 in order to prevent undesirable egress of irrigation fluid as hereinabove discussed. Dependent members 88, 90 are also provided within the sleeve 116 and function in a manner identical to the members 88, 90, shown in FIGS. 4 and 5.

Although there has been hereinabove described specific embodiments of phaco tip apparatus, in accordance with the present invention, for the purpose of illustrating the manner in which the invention may be used to advantage, it should be appreciated that the invention is not limited thereto. Accordingly, any and all embodiments, variations, or equivalent arrangements which may occur to those skilled in the art, should be considered to be within the scope of the present invention as defined in the appended claims.

What is claimed is:

1. A phaco tip apparatus for a phacoemulsification handpiece having vibration drive assembly, said phaco tip apparatus comprising:

a needle having a tip for emulsifying a cataract lens through a cornea/sclera wound;

a lumen through the tip and providing a primary aspiration port to the needle for the aspiration of emulsified lens;

a sleeve for establishing an annular passage around the needle and enabling irrigation fluid to pass into an eye through the cornea/sclera wound while cooling the needle, said sleeve having a length shorter than a length of the needle;

a secondary aspiration port disposed in said needle between the needle end and the sleeve for enabling continued aspiration of emulsified lens upon clogging of the primary aspiration port; and a bypass port, disposed in said needle and under said compressible sleeve, for establishing fluid communication between said lumen and said annular passage in order to enable irrigation fluid to pass into said lumen upon clogging of the primary and secondary aspiration ports.

2. The phaco tip apparatus according to claim 1 wherein said sleeve is compressible.

3. The phaco tip apparatus according to claim 1 wherein a cross-sectional area of said secondary aspiration port is between about 5% and about 15% of the cross-sectional area of said lumen.

4. The phaco tip apparatus according to claim 3 wherein a cross-sectional area of said bypass port is between about 5% and about 15% of the cross-sectional area of said lumen.

5. The phaco tip apparatus according to claim 4 where the secondary aspiration port cross-sectional area is between 5% and 15% of the bypass port cross-sectional area.

6. Phaco tip apparatus for a phacoemulsification handpiece having vibration drive assembly, said phaco tip apparatus comprising:

a needle having a tip for emulsifying a cataract lens through a cornea/sclera wound;

a lumen through the tip and providing a primary aspiration port in an end of the needle for the aspiration of emulsified lens;

a compressible sleeve for establishing an annular passage around the needle and enabling irrigation fluid to pass into an eye through the cornea/sclera wound while cooling the needle, said compressible sleeve having a length shorter than a length of the needle;

a secondary aspiration port disposed in said needle between the needle end and the sleeve for enabling continued aspiration of emulsified lens upon clogging of the primary aspiration port;

a bypass port, disposed in said needle and under said compressible sleeve, for establishing fluid communication between said lumen and said annular passage in order to enable irrigation fluid to pass into said lumen upon clogging of the primary and secondary aspiration ports; and a depending member disposed within said compressible sleeve for limiting compression of opposing walls of said compressible sleeve in order to prevent contact of said compressible sleeve with said needle, maintain the annular passage flow of irrigation fluid past said needle and prevent the compressible sleeve from closing said bypass port.

7. The phaco tip apparatus according to claim 6 wherein a cross-sectional area of said secondary aspiration port is between about 5% and about 15% of the cross-sectional area of said lumen.

8. The phaco tip apparatus according to claim 7 wherein a cross-sectional area of said bypass port is between about 5% and about 15% of the cross-sectional area of said lumen.

9. The phaco tip apparatus according to claim 8 wherein the secondary aspiration port cross-section is between about 5% and 15% of the bypass port cross-section.

* * * * *